United States Patent [19]

Coon

[11] 4,022,825
[45] May 10, 1977

[54] IMIDOL ISOMER OF N-CHLOROFORMAMIDO AND ITS PROCESS OF PREPARATION

[75] Inventor: Clifford L. Coon, Menlo Park, Calif.

[73] Assignee: Koppers Company, Inc., Pittsburgh, Pa.

[22] Filed: July 16, 1973

[21] Appl. No.: 379,768

[52] U.S. Cl. .......................................... 260/543 A
[51] Int. Cl.² ..................................... C07C 119/18
[58] Field of Search ....... 260/543 A, 561 R, 566 D, 260/453 R

[56] References Cited

UNITED STATES PATENTS 2,640,846  6/1953  Hurwitz et al. ................ 260/561 R
2,971,959  2/1961  Waugh et al. ................ 260/326 HL

OTHER PUBLICATIONS

Leipert—C.A. vol. 32(1938), 8620[9].

Primary Examiner—Lorraine A. Weinberger
Assistant Examiner—Lisa Jones
Attorney, Agent, or Firm—Herbert J. Zeh, Jr.; Oscar B. Brumback

[57] ABSTRACT

The composition of matter of N-chloroformamide is disclosed along with a method for preparing the same. The N-chloroformamide normally exists in its tautomeric imidol form. The N-chloroformamide readily reacts with amines to form substituted ureas.

2 Claims, No Drawings

IMIDOL ISOMER OF N-CHLOROFORMAMIDO AND ITS PROCESS OF PREPARATION

BACKGROUND OF THE INVENTION

This invention is directed to the composition of matter of N-chloroformamide. It is also directed to a method for preparing the same and to the reaction of N-chloroformamide with amines to form substituted ureas.

Heretofore, the compound N-chloroformamide has been unreported in the literature. The compound N,N-dichloroformamide has been reported. The dichloro compound is formed by the aqueous chlorination of formamide. See, for example, P. L. Magill, Industrial and Engineering Chemistry, 26,611 (1934). The compounds N-bromoformamide and N-iodoformamide may be prepared by reacting the appropriate halogen with formamide in the presence of silver oxide. These compounds are reported in Kirk Othmer, Encyclopedia of Chemical Technology, Volume 10. In addition, see E. Boismenu, Compt. Rend. Vol. 53, at 678, 948 and 1482 (1911) which are directed to the halogen substituted formamides. However, the compound N-chloroformamide has not heretofore been made or reported.

SUMMARY OF THE INVENTION

I have discovered the composition of matter of N-chloroformamide and a method for preparing the same. The composition of N-chloroformamide has been identified by infrared analysis, nuclear magnetic resonance and elemental analysis. The composition is represented by the formula:

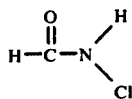

The ir and nmr analysis indicate that the compound exists under normal conditions in the more stable tautomeric imidol form which is represented by the formula:

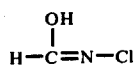

I have prepared N-chloroformamide in its imidol form by reacting formamide with t-butylhypochlorite in an organic solvent. The method of my invention comprises reacting approximately equal molar amounts of formamide and t-butylhypochlorite in an organic solvent. The resulting imidol of N-chloroformamide may then be isolated by evaporating the solvent or by filtration if the N-chloroformamide is insoluble in that particular solvent.

N-chloroformamide is a small one carbon molecule which is relatively inexpensive to prepare. It has great value as a chemical intermediate. I have reacted N-chloroformamide with olefins, bases, alcohols and amines. The reaction of N-chloroformamide with amines provides a unique and excellent process for preparing substituted ureas.

The following examples are illustrative of the preparation and use of N-chloroformamide. They should be construed to illustrate the invention, but not to limit the same.

EXAMPLE 1

Preparation of N-chloroformamide

Ten grams of formamide (0.22 mol) was stirred in 20 ml of methylene chloride at a temperature of 5°–10° C. Then 24.0 gm of t-butylhypochlorite (0.22 mol) was added dropwise over a twenty minute period while maintaining the temperature of about 5°–10° C. The methylene chloride solvent was removed under vacuum leaving about 18 grams of a soft white solid that was immediately taken up in 20 ml of chloroform and cooled. Then white plate-like crystals were formed and collected by filtration. The crystals were dried over phosphorus pentoxide to give 12.61 gms of product. An additional 3.53 gms of product was collected by evaporating the filtrate to half volume and recooling. The total amount of product recovered was 16.16 gms (91%). The product was analyzed and identified as the tautomeric imidol form of N-chloroformamide by elemental analysis, infrared spectra and nuclear magnetic resonance spectra. The compound was very corrosive and a molecular weight was not obtained. The results of the analysis are shown below:

Elemental Analysis for $CH_2ClNO$: Calculated: C=15.10%; H=2.54%; Cl=44.61%; N=17.62%; Found: C=15.01%; H=2.40%; Cl=44.58%; N=17.81%.

Infrared Analyses (Nujol): 3.3–3.5 (s) OH; 3.80 (w) CH; 6.04 (s), 6.13 (s) C=N; 6.9 (m), 7.34 (s), 8.39 (w), 8.50 (w), 10.52 (w), 11.8 (w) 14.6 (m).

| Nuclear Magnetic Resonance ($CDCl_3$) | |
|---|---|
| Chemical Shift | Assignment |
| 1.67 γ sharp singlet | Cl N=CHOH |
| 1.8 γ broad singlet | Cl N=CHOH |

The N-chloroformamide product formed large white plate-like crystals which had a melting point of 59°–60° C. The compound possesses an odor similar to that of a sodium hypochlorite and decomposes slowly at room temperature.

EXAMPLE 2

Reaction of N-chloroformamide with n-butylamine

A solution of 0.94 gm (12.6 m mol) of n-butylamine in 10 ml of methylene chloride was prepared. The temperature of the solution was 25° C. Then 0.50 gm (6.3 m mol) of N-chloroformamide in 5 ml of methylene chloride was added over a ten minute period. Slight cooling was needed with an ice bath to keep the reaction temperature at 25° C. The reaction mixture was then stirred for six hours during which time a brown solid separated from solution. The solvent was removed under vacuum leaving 1.43 gms of a brown solid which was triturated with eight 20 ml portions of ether. The ether portions were combined, and the solvent removed leaving 0.61 (84%) of a white crystalline solid which was identified as N-butylurea by its melting point (94°–95° C), ir spectrum, and elemental analysis. The ether insoluble material was shown to contain n-butylamine hydrochloride by its ir spectrum.

EXAMPLE 3

Reaction of N-chloroformamide with cyclohexene

A mixture of 1.50 gm (18.9 m mol) of N-chloroformamide and 10.0 gm of cyclohexene was stirred at ambient temperature for 17 hours during which time a sticky orange solid formed. The light orange liquid was decanted and the solid dried under vacuum oven $P_2O_5$ to give a light brown solid weighing 0.71 gm and having a m.p. of 158°–160° C. After two recrystallizations from ethanol it weighed 0.58 gm. The ir spectrum of this material contained HN, OH absorptions and small carbonyl absorptions. The decanted liquid was evaporated leaving 1.46 g of an orange liquid which by vpc analysis was shown to contain three major and four minor components. The three major components were isolated by preparative vpc techniques and identified as trans-1-2-dichlorocyclohexane, trans-1-hydroxy-2-chlorocyclohexane, and 2 chloro-1-cyclohexylformate by comparison of their ir spectra with those of authentic samples. The formation of 2-chloro-1-cyclohexylformate illustrates the simple addition product of N-chloroformamide with cyclohexane. This would be expected of N-chloroformomamide.

I claim:

1. The tautomeric imidol isomer of N-chloroformamide repesented by the formula

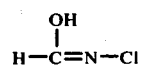

2. A method for preparing the imidol isomer of N-Chloroformamide comprising reacting formamide with t-butylhypochloride in an organic solvent.

* * * * *

UNITED STATES PATENT OFFICE
CERTIFICATE OF CORRECTION

PATENT NO. : 4,022,825
DATED : May 10, 1977
INVENTOR(S) : Clifford L. Coon

It is certified that error appears in the above-identified patent and that said Letters Patent are hereby corrected as shown below:

In the Title: N-Chloroformamido should be N-Chloroformamide

Column 4, line 17, delete t-butylhypochloride and insert t-butylhypochlorite.

Signed and Sealed this twelfth Day of July 1977

[SEAL]

Attest:

RUTH C. MASON
Attesting Officer

C. MARSHALL DANN
Commissioner of Patents and Trademark